United States Patent
Baker et al.

(10) Patent No.: US 7,709,596 B2
(45) Date of Patent: May 4, 2010

(54) CYCLIC ALKYL SUBSTITUTED GLYCOLIDES AND POLYLACTIDES THEREFROM

(75) Inventors: Gregory L. Baker, Haslett, MI (US); Feng Jing, Atlanta, GA (US); Milton R. Smith, III, East Lansing, MI (US)

(73) Assignee: Board of Trustees of Michigan State University, East Lansing, MI (US)

(*) Notice: Subject to any disclaimer, the term of this patent is extended or adjusted under 35 U.S.C. 154(b) by 0 days.

(21) Appl. No.: 12/583,635

(22) Filed: Aug. 24, 2009

(65) Prior Publication Data

US 2010/0041902 A1 Feb. 18, 2010

Related U.S. Application Data

(62) Division of application No. 11/639,760, filed on Dec. 15, 2006, now Pat. No. 7,579,429.

(60) Provisional application No. 60/751,403, filed on Dec. 16, 2005.

(51) Int. Cl.
$C08G\ 69/08$ (2006.01)
(52) U.S. Cl. ..................... 528/310
(58) Field of Classification Search ............. 528/310
See application file for complete search history.

(56) References Cited

U.S. PATENT DOCUMENTS 6,469,133 B2 10/2002 Baker et al.

FOREIGN PATENT DOCUMENTS

WO WO 99/55692 11/1999

OTHER PUBLICATIONS

Edlund, U., Albertsson, A. Adv. Polym. Sci. 2001, 157, 67.
Mecking, S., Angew. Chem. Int. Ed. 2004, 43, 1078.
Lou, X., Detrembleur, C., Jerome, R. Macromol. Rapid Commun. 2003, 24, 161.
Ikada, Y., Tsuji, H. Macromol. Rapid Commun. 2000, 21, 117.
Cabaret, O., Marin-Vaca, B., Bourissou, D. Chem. Rev. 2004, 104, 6147.
Auras, R, Harte, B., Selke, S. Macromol. BioSci. 2004, 4, 835.
Drumright, R., Gruber, P., Henton, D. Adv. Mater. 2000, 12, 1841.
Chiellini, E., Solaro, R. Adv. mater. 1996, 8, 305.
Zhang, F., Xu, J., Alcazar-Roman, L., Greenman, L., Cramer, C., Hillmyer, M., Toman, W. Macromolecules 2004, 37, 5274.
Hu, Y., Rogunova, M., Topolkaraev, V., Hltner, A., Baer, E. Polymer 2003, 44, 5701.
Zhong, A., Dijkstra, R., Feijen, J. J. Am. Chem. Soc. 2003, 125, 11291.
Radano, C., Baker, G., Smith, M.J. Am. Chem. Soc. 2000, 122, 1552.
Tasaka, R., Ohya, Y., Ouchi, T. Macromolecules 2001, 34, 5494.

(Continued)

*Primary Examiner*—Randy Gulakowski
*Assistant Examiner*—Shane Fang
(74) *Attorney, Agent, or Firm*—Ian C. McLeod; Steven M. Parks (57) ABSTRACT

Cyclic alkyl, particularly cyclohexyl, substituted glycolides and polylactides are described. The polylactides have a high glass transition temperature and improved clarity.

9 Claims, 8 Drawing Sheets

OTHER PUBLICATIONS

Ouchi, T., Minari, T., Ohya, Y. J. Polym. Sci, Polym. Chem. 2004, 42, 5482.
Gadzinowski, M., Sosnowski, S.J. Polym. Sci, Polym. Chem. 2003, 41, 3750.
Yin, M., Baker, G.L. Macromolecules 1999, 32, 7711.
Simmons, T., Baker, G. Biomacromolecules 2001, 2, 658.
Liu, T., Simmons, T., Baker, G., Polym. Mater. Sci. Eng. 2003, 88, 420.
Trimaille, T., Moller, M., Gurny, R., J. Polym Sci., Polym. Chem. 2004, 42, 4379.
Nederberg et al., Angew Chem Int. Ed 40 2712-2715 (2001).
Yang et al., Chinese Journal of Polymer Science 20 413-417 (2002).
Yang et al., Chinese Journal of Polymer Science 19 509-516 (2001).
Mori, K., Takaishi, H. Tetrahedron 1989, 45, 1639.
Riley, D., Shumate, R. J. Org. Chem. 1980, 45, 5187.
Stocker, J.H., J. Org. Chem. 1962, 27, 2288.
Witzke, D., Narayan, R., Macromolecules 1997, 30, 7075.
Kowalski, A., Duda, A., Penczek, S. Macromolecules 2000, 33, 7359.
Zhang, J., Sato, H., Tsuji, H., Noda, I., Ozaki, Y. Macromolecules 2005, 38, 1822.
Cao, C., Lin, Y.J. Chem. Inf. Comput. Sci. 2003, 43, 643.
Zhao, J., Hanh, S., Hucul. D., Meunier, D., Macromolecules 2001, 34, 1737.
Zell, M., Padden, B., Paterick, A., Thakur, K., Kean, R., Hillmyer, M., Munson, E., Macromolecules 2002, 35, 7700.
Chisholm, m., Iyer, S., McCollum, D., Pagel, M., Werner-Zwanziger, U., Macromolecules 1999, 32, 963.
Coudane, J., Ustariz-Peyret, C., Schwach, G., Vert, J., J. Polym. Sci., Polym. Chem. 1999, 35, 1651.
Kasperczyk, J. Polymer 1999, 40, 5455.
Thakur, K., Kean, R., Hall, E., Kolstad, J., Munson, E., Macromolecules 1998, 31, 1487.
Thakur, J., Kean, R., Hall, J., Kolstad, J., Lindgren, T., Doscotch, M., Siepmann, J., Muson, E., Macromolecules 1997, 30, 2422.
Pure and Applied Chemistry 68, 2287-2311 (1996).
Pure Applied Chemistry 53, 733-752 (1981).
Ovitt, T.M., Coates, G.W., J.Am.Chem.Soc. 2002, 124, 1316.
Csiborg et al., J.Am.Chem.Soc. 127 9079-9084(2005).
Nishida, H., Mori, T., Hoshihara,S., Fan, Y., Shirai, Y., Endo, T., Polym. Degrad.Stab.2003, 81,515.

CYCLIC ALKYL SUBSTITUTED GLYCOLIDES AND POLYLACTIDES THEREFROM

CROSS-REFERENCE TO RELATED APPLICATIONS

This application claims benefit to U.S. Provisional Application Ser. No. 60/751,403, filed Dec. 16, 2005, and is a division of U.S. application Ser. No. 11/639,760, Filed Dec. 15, 2006, now U.S. Pat. No. 7,759,429 both of which are incorporated herein by reference in their entireties.

STATEMENT REGARDING FEDERALLY SPONSORED RESEARCH OR DEVELOPMENT

Not Applicable

STATEMENT REGARDING GOVERNMENT RIGHTS

Not Applicable

BACKGROUND OF THE INVENTION (1) Field of the Invention

The present invention relates to cyclic alkyl substituted glycolides which are used to prepare polylactide polymers. The polymers are characterized by having higher glass transition temperatures and better clarity than prior art polylactide polymers.

(2) Description of the Related Art

High molecular weight aliphatic polyesters, a class of biodegradable and biocompatible polymers, have emerged as potential environmentally friendly replacements for current commodity polymers (Edlund, U., Albertsson, A. Adv. Polym. Sci. 2001, 157, 67; Mecking, S., Angew. Chem. Int. Ed. 2004, 43, 1078; Lou, X.; Detrembleur, C.; Jerome, R. Macromol. Rapid Commun. 2003, 24, 161; and Ikada, Y., Tsuji, H. Macromol. Rapid Commun. 2000, 21, 117)). Of these, polylactide is one of the most widely utilized polyesters (Cabaret, O.; Martin-Vaca, B.; Bourissou, D. Chem. Rev. 2004, 104, 6147; Auras, R.; Harte, B., Selke, S. Macromol. BioSci. 2004, 4, 835; and Drumright, R.; Gruber, P.; Henton, D. Adv. Mater. 2000, 12, 1841)) because of its biocompatibility and biodegradability, high mechanical strength, and excellent shaping and molding properties (Auras, R.; Harte, B; Selke, S., Macromol. BioSci. 2004, 4, 835 and Chiellini, E.; Solaro, R. Adv. Mater. 1996, 8, 305)). However, the relatively low glass transition temperature ($T_g$) of polylactide limits its use as a rigid, clear replacement for large-volume thermoplastics such as polystyrene. Crystallinity is commonly used to increase the use temperature of polylactides, but at the cost of substantially decreased degradation rate. To be suitable for different applications, polylactides must exhibit a broader range of physical properties while retaining the degradability of the parent polymer. Typical approaches used to alter the physical properties of polylactides include improving ductility, (Zhang, F.; Xu, J.; Alcazar-Roman, L.; Greenman, L.; Cramer, C.; Hillmyer, M.; Tolman, W. Macromolecules 2004, 37, 5274 and Hu, Y.; Rogunova, M.; Topolkaraev, V.; Hiltner, A.; Baer, E. Polymer 2003, 44, 5701)) manipulating tacticity, (Ovitt, T. M.; Coates, G. W., J. Am. Chem. Soc. 2002, 124, 1316 and Zhong, A.; Dijkstra, R.; Feijen, J. J. Am. Chem. Soc. 2003, 125, 11291)) altering crystallinity, (Radano, C.; Baker, G.; Smioth, M. J. Am. Chem. Soc. 2000, 122, 1552 and Tasaka, R.; Ohya, Y.; Ouchi, T. Macromolecules 2001, 34, 5494)) and increasing hydrophilicity (Ouchi, T.; Minari, T.; Ohya, Y. J. Polym. Sci., Polym. Chem. 2004, 42, 5482 and Gadzinowski, M; Sosnowski, S. J. Polym. Sci., Polym. Chem. 2003, 41, 3750)). In contrast, there are few reports of polylactide derivatives where the methyl groups of lactide were replaced by other alkyl or functional groups (Yin, M.; Baker, G. L. Macromolecules 1999, 32, 7711; Simmons, T.; Baker, G. Biomacromolecules 2001, 2, 658; Liu, T.; Simmons, T.; Baker, G. Polym. Mater. Sci. Eng. 2003, 88, 420 and Trimaille, T.; Moller, M.; Gurny, R., J. Polym Sci., Polym. Chem. 2004, 42, 4379)). Simple changes to the substituents on the lactide ring could provide routes to polymers with controlled hydrophobicities, glass transition temperatures, and provide polylactides with new chemical functionality.

The glass transition temperatures of most lactide homopolymers and copolymers are <60° C. It is well known that increasing the rigidity of polymer chains leads to higher $T_g$s and improved dimensional stability at high temperatures. Taking a cue from polyolefins, the rigidity of the polylactide chain can be increased by simply replacing the methyl groups with bulky groups, such as phenyl. Previously we reported that polymerization of 3,6-diphenyl-1,4-dioxane-2,5-dione (mandelide, Scheme 1) yields high molecular weight polymers with $T_g$>100° C. (Liu, T.; Simmons, T.; Baker, G., Polym. Mater. Sci. Eng. 2003, 88, 420). However, the synthesis of mandelide is problematic. Two diastereomers form when mandelic acid is dimerized. Of these, meso-mandelide (R,S-mandelide) can be polymerized under bulk or solution polymerization conditions, while rac-mandelide (an equal molar mixture of R,R-mandelide and S,S-mandelide) is insoluble in common solvents and decomposes before melting. Furthermore, meso-mandelide is less stable than rac-mandelide, and readily transforms to rac-mandelide by deprotonation of the methine protons during purification. In addition, the lability of the methine protons fosters thermal and photochemical degradation which leads to discoloration during melt processing.

The preparation of polymers from glycolides (dimeric cyclic esters is described in U.S. Pat. No. 6,469,133 to Baker and Smith, two of the present inventors. The disclosure of this patent is incorporated in its entirety herein. There is still a need for improved glycolides and polymers therefrom, particularly in the clarity and other properties, such as the glass transition temperature.

OBJECTS

It is therefore an object of the present invention to provide improved glycolides and polymers therefrom as well as a process for preparing them. It is further an object to provide a process which is economical and effective to produce these polymers. These and other objects will become increasingly apparent by reference to the following description and the drawings.

SUMMARY OF THE INVENTION

The present invention relates to a glycolide compound of the formula:

wherein R is selected from the group consisting of hydrogen and lower alkyl containing 1 to 8 carbon atoms and cycloalkyl containing 3 to 8 carbon atoms, where optionally R is substituted with a first passive substituent and $R_1$ is hydrogen or a second passive substituent. Preferably R is cyclohexyl and R1 is hydrogen. Preferably R is methyl or isopropyl, and R1 is hydrogen. Preferably the glycolide is an enantiomer selected from the group consisting of RR, SS and RS isomers. Preferably R is cyclohexyl as an RR-dicyclohexylglycolide enantiomer. Preferably R is cyclohexyl as an SS dicyclohexylglycolide enantiomer. Preferably R is cyclohexyl as a racemic RS dicyclohexylglycolide.

The present invention also relates to a polymer of a polymerized glycolide compound of the formula and mixtures thereof, where R is selected from the group consisting of hydrogen and lower alkyl containing 1 to 8 carbon atoms and cycloalkyl containing 3 to 8 carbon atoms where optionally R is substituted with passive substituents and $R_1$ is hydrogen or the passive substituent. Preferably R is cyclohexyl and $R_1$ is hydrogen. Preferably R is methyl or isopropyl and $R_1$ is hydrogen. Preferably the glycolide compound which is an enantiomer selected from the group consisting of RR, SS and RS isomers. Preferably R is cyclohexyl as a polymerized RR-dicyclohexylglycolide enantiomer. Preferably R is cyclohexyl as a polymerized SS dicyclohexylglycolide enantiomer. Preferably R is cyclohexyl as a polymerized racemic RS-dicyclohexylglycolide.

The present invention also relates to a polymer of a polymerized mixture of glycolide compounds with different R wherein the glycolide is of the formula:

wherein R is selected from the group consisting of hydrogen and lower alkyl containing 1 to 8 carbon atoms and cycloalkyl containing 3 to 8 carbon atoms, where optionally R is substituted with a first passive substituent and $R_1$ is hydrogen or a second passive substituent.

The present invention also relates to a process for the preparation of a polymer of a glycolide compound of the formula:

wherein R is selected from the group consisting of hydrogen and lower alkyl containing 1 to 8 carbon atoms and cycloalkyl containing 3 to 8 carbon atoms, where optionally R is substituted with a first passive substituent and $R_1$ is hydrogen or a second passive substituent, which comprises reacting the glycolide compound with at least one compound which is a catalyst and reaction initiator in a non-reactive solvent polymerization solvent or in a melt polymerization to produce the polymer. Preferably the catalyst is tin (II) 2-ethylhexanoate and the initiator is 4-tert-butyl benzyl alcohol. Preferably the reaction is at a temperature above about 60° C. up to the degradation temperature of the monomer. Preferably R is cyclohexyl. Preferably R is methyl or isopropyl. Preferably the reacting glycolide is selected from the group consisting of RR, SS and RS isomers. Preferably R is cyclohexyl and comprising an RR-dicyclohexylglycolide enantiomer in the reaction. Preferably R is cyclohexyl comprising an SS dicyclohexylglycolide enantiomer in the reaction. Preferably R is cyclohexyl comprising racemic RS dicyclohexylglycolide in the reaction.

Various catalysts are known in the art for ring opening polymerizations (ROP). These include strongly basic amines, such as 4-(N,N-dimethylamino)pyridine (DMAP) described by Nederberg et al. Angew Chem. Int. Ed 40 2712-2715 (2001); N-heterocyclic carbenes (NHCs) described by Csiborg et al., J. Am. Chem Soc 127 9079-9084 (2005); metal organic catalysts such as Sn(II) 2-ethylhexonate (Sn(Oct)$_2$ as described by Yang et al. Chinese Journal of Polymer Science 20 413-417 (2002) and 19 509-516 (2001). Also Baker and Smith in the '133 patent describe catalysts for such reactions. The ring opening polymerization catalysts are known to those skilled in the art.

The cyclohexyl substituted α-hydroxyacids used to form the glycolides can be derived as follows:

phenylalanine with
$R_1$ which can be OH
(protected)

-continued cyclohexyl
group with R₁

The R and R₁ groups on the glycolides can be substituted with groups which do not interfere with the polymerization, i.e. are passive groups. In particular, protected hydroxyl groups can be present on the glycolides for polymerization, such as benzyloxy groups (Su Yang et al cited previously). Once the polymer is prepared, the hydroxyl group can be deprotected to a hydroxyl group which can be used for further reactions of the polymer. The R groups can be a lower alkyl containing 1 to 8 carbon atoms and cycloalkyl containing 3 to 8 carbon atoms.

DESCRIPTION OF PREFERRED EMBODIMENTS

In particular the present invention describes the solution and bulk polymerization of rac-dicyclohexylglycolide (rac-3,6-dicyclohexylglycolide-1,4-dioxane-2,5-dione), and rac-diisopropylglycolide (rac-3,6-diisopropyl-1,4-dioxane-2,5-dione) and rac-methylcyclohexylglycolide (rac-3-cyclohexyl-6-methyl-1,4-dioxane-2,5-dione). Of these monomers, the solution polymerization rate of rac-dicyclohexylglycolide is the slowest. This is attributed to steric shielding of the glycolide ester by the bulky cyclohexyl group. This steric hindrance leads to a very high glass transition temperature of poly(rac-dicyclohexylglycolide) at 98° C. Meso-Dicyclohexylglycolide and R,R-dicyclohexylglycolide were synthesized and polymerized to determine the effect of stereochemistry on the polymer properties.

Results

EXAMPLES

Monomer Synthesis. The α-hydroxy acids used to prepare substituted glycolide monomers were commercial products or in the case of 2-cyclohexyl-2-hydroxyacetic acid and 2-hydroxy-3-methyl butyric acid, synthesized from naturally occurring α-hydroxyacids and amino acids. Diazotization of DL-valine (Mori, K.; Takaishi, H. Tetrahedron 1989, 45, 1639) provided 2-hydroxy-3-methyl butyric acid while hydrogenation of mandelic acid using a rhodium on carbon catalyst yielded 2-cyclohexyl-2-hydroxyacetic acid (Scheme 2) (Riley, D.; Shumate, R. J. Org. Chem. 1980, 45, 5187 and Stocker, J. H.; J. Org. Chem. 1962, 27, 2288)). The conversion of α-hydroxyacids to symmetric and non-symmetric glycolides followed two previously reported synthetic protocols, (Yin, M.; Baker, G. L.; Macromolecules 1999, 32, 7711 and Baker, G. and Smith, M.; U.S. Pat. No. 6,469,133))(Scheme 3). The first was acid-catalyzed dimerization of the α-hydroxy acids in toluene with the water removed by azeotropic distillation. Run in dilute solution to favor formation of the symmetric dimers over linear oligomers, a mixture of the R,S (meso) and R,R/S,S (rac) diastereomers was obtained in 20-40% yield. To prepare the nonsymmetric methyl cyclohexyl glycolide, 2-cyclohexyl-2-hydroxyacetic acid was condensed with 2-bromopropionyl bromide. This route favors the formation of racemic products, with the meso diastereomer as a minor component.

Scheme 1

Glycolide          Lactide

Mandelide

Dicyclohexylglycolide (1)

Diisopropylglycolide (2)

Methylcyclohexylglycolide (3)

Scheme 2

Scheme 3

Figure 1:
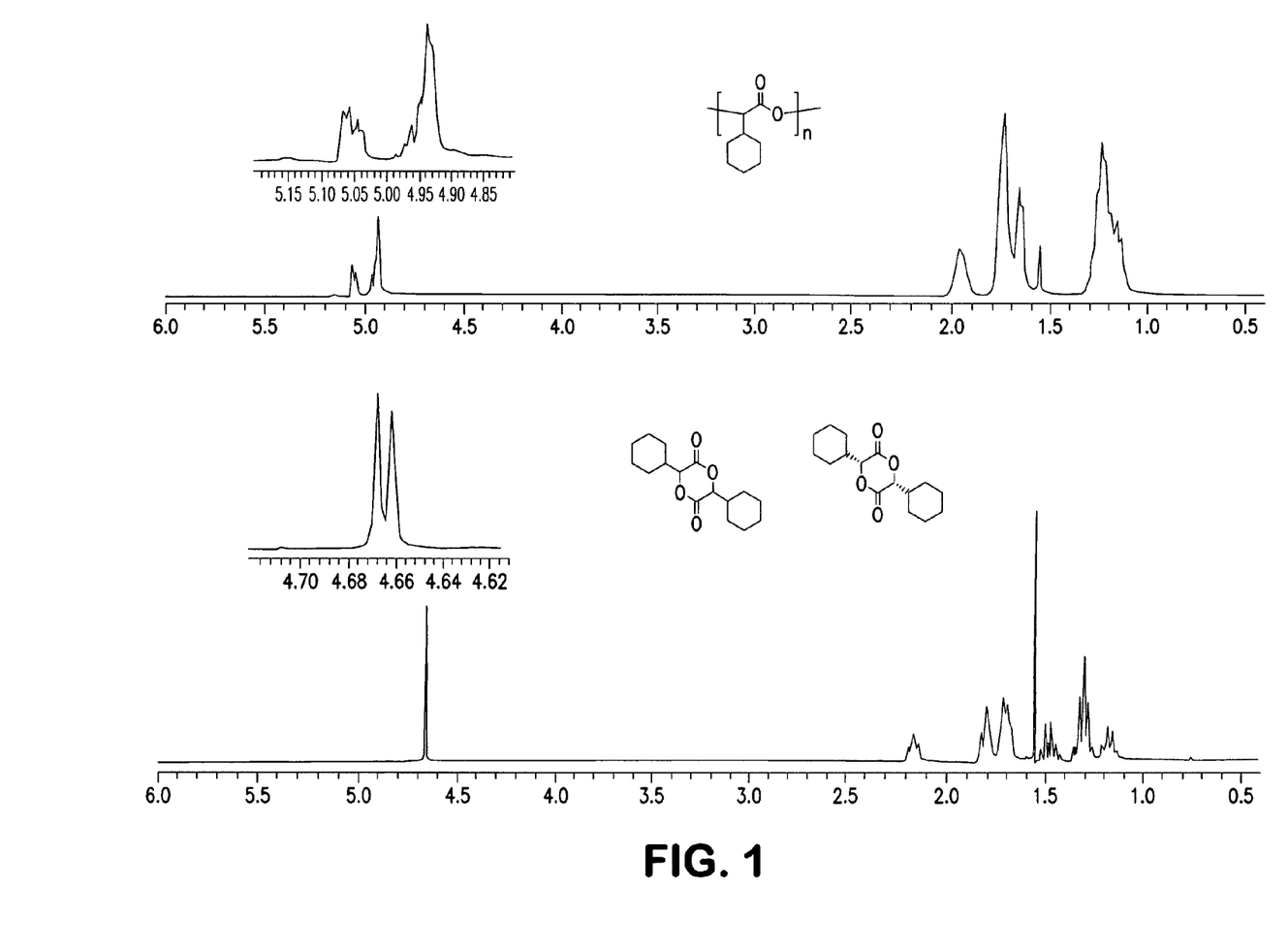
FIG. 1 is a graph showing $^1$H NMR spectra for rac-dicyclohexylglycolide and poly(rac-dicyclohexylglycolide).

To compare the effects of different substituents on polymer properties and polymerization kinetics, we polymerized glycolides substituted with methyl, isopropyl and cyclohexyl groups. For consistency, all polymers were prepared from racemic glycolides that had been purified by recrystallization and/or column chromatography to remove meso contaminants. Representative NMR spectra of rac-dicyclohexylglycolide and its polymer are shown in FIG. 1. The $^1$H NMR spectrum of the monomer shows the expected doublet for the methine protons at 4.66 ppm and no evidence for contamination from the meso diastereomer (Yin, M.; Baker, G. L.; Macromolecules 1999, 32, 7711). After polymerization, the signals from the methine protons broaden and shift downfield to 4.94 ppm and 5.06 ppm, allowing simple calculation of conversion from the integrated intensities of the monomer and polymer methine signals.

Solution Polymerization Kinetics. Solution polymerizations of racemic glycolides using Sn(2-ethylhexanoate)$_2$ as the catalyst and 4-tert-butylbenzyl alcohol (BBA) as the initiator were carried out in toluene to evaluate the effect of the size of glycolide ring substituents on the rate of polymerization. Ring-opening polymerizations of lactide derivatives typically follow first-order kinetics for low conversion when initiated by alcohols and catalyzed by Sn(2-ethylhexanoate)$_2$ (Yin, M.; Baker, G. L.; Macromolecules 1999, 32, 7711; Witzke, D.; Narayan, R., Macromolecules 1997, 30, 7075; and Kowalski, A.; Duda, A.; Penczek, S. Macromolecules 2000, 33, 7359)). For polymerizations at 90° C. with relatively low monomer concentrations (~0.2 M) and initiator and catalyst loadings (1 mol %), conversion is easily controlled, depolymerization is negligible, and the polymerization can be treated as an irreversible reaction (Witzke, D.; Narayan, R.; Macromolecules 1997, 30, 7075) as expressed in equation 1

$$R = -\frac{d[M]}{dt} = k_p[M][I] \tag{1}$$

where [M] and [I] are the concentration of monomer and initiator respectively, and $k_p$ is the apparent rate constant for propagation. For a living polymerization, [I] is a constant, and plots of $-\ln([M]_t/[M]_0)$ versus time t should be linear with slope $k_p[I]$, where $[M]_t$ is the concentration of the monomer at time t and $[M]_0$ is the initial monomer concentration

TABLE 1

Solution Polymerization Rates of Glycolides

| Monomer | $k_p$ (L · s$^{-1}$ · mol$^{-1}$) × 10$^3$ |
| --- | --- |
| rac-lactide | 9.87 |
| rac-methylcyclohexylglycolide | 1.38 |
| rac-diisopropylglycolide | 0.528 |
| rac-dicyclohexylglycolide | 0.139 |

Figure 2:
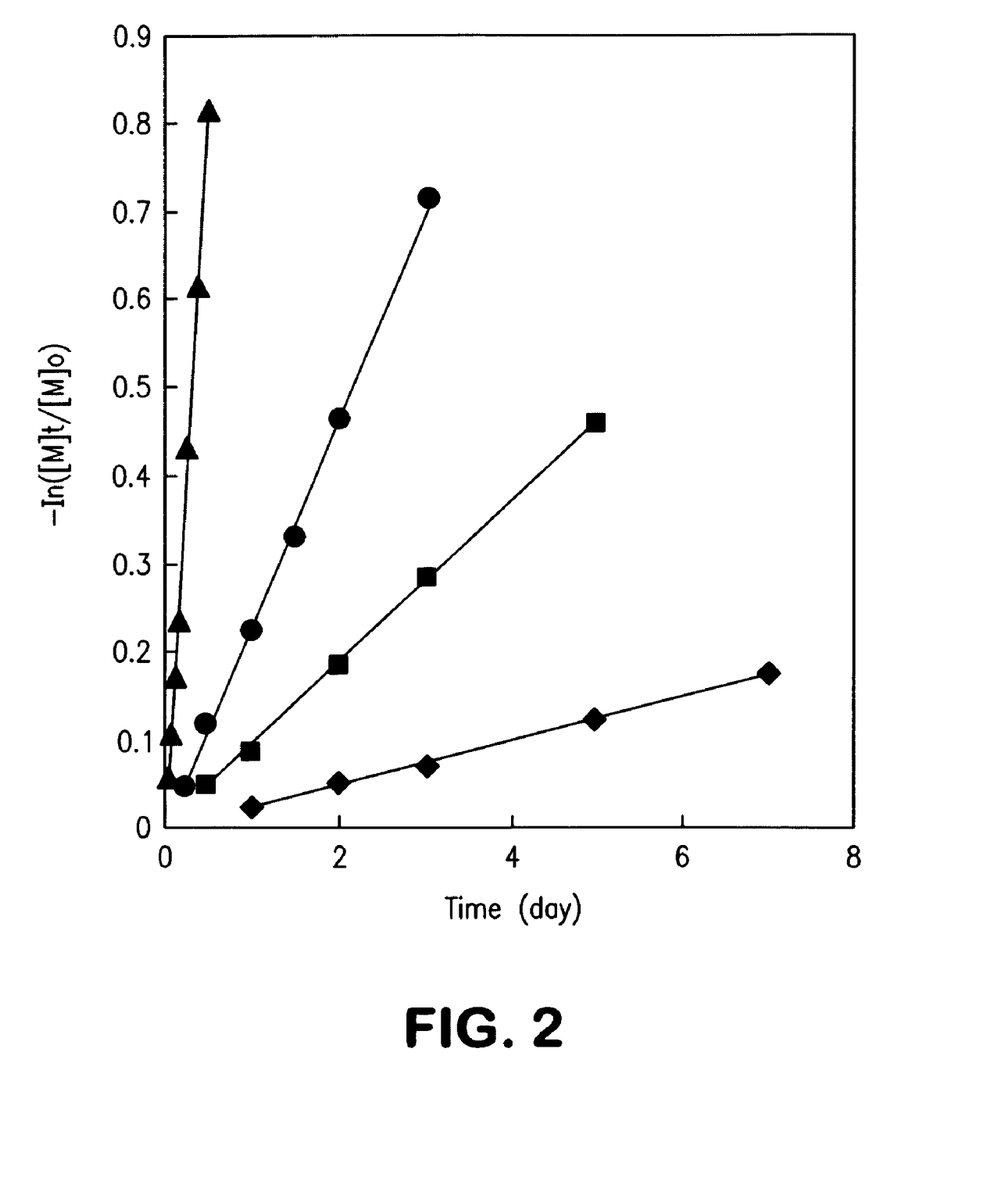
FIG. 2 is a graph showing kinetics of solution polymerization of rac-lactide (▲), rac-diisopropylglycolide (■), rac-methylcyclohexylglycolide (●), and rac-dicyclohexylglycolide (♦). Polymerization conditions: 90° C., [Sn(2-ethylhexanoate)₂]/[4-tert-butylbenzyl alcohol]=1, [monomer]/[catalyst]=100.

The data shown in FIG. 2 are consistent with simple first order kinetics. As expected, the polymerization rates (Table 1) depended on the size of the glycolide ring substituents, with the polymerization of rac-dicyclohexylglycolide the slowest, 1/70$^{th}$ of the rate for the polymerization of rac-lactide. While the isopropyl group should be a reasonable mimic for the cyclohexyl group, the polymerization rate of rac-diisopropylglycolide is 4× faster than that of rac-dicyclohexylglycolide. The results for rac-methylcyclohexylglycolide are particularly interesting. The polymerization rate is ~10× that of rac-dicyclohexylglycolide, implying preferential ring opening at the carbonyl adjacent to methyl group and an alternating sequence of methyl and cyclohexyl groups along the polymer backbone.

Polymer Properties. Polymer properties were measured using materials prepared by bulk polymerizations with a monomer to initiator ratio of 300. The crude polymers were purified by

TABLE 2

Properties of Polyglycolides

| Polymer | $M_n \times 10^{-3}$ | $M_w/M_n$ | $T_g$ (° C.) |
|---|---|---|---|
| poly(rac-lactide) | 82.9 | 1.39 | 55 |
| poly(rac-diisopropylglycolide) | 89.3 | 1.18 | 41 |
| poly(rac-methylcyclohexylglycolide) | 40.5 | 1.27 | 73 |
| Poly(rac-dicyclohexylglycolide) | 99.3 | 1.38 | 98 | precipitation into cold methanol to remove monomers, washed with dilute HCl to remove catalyst residues, and then dried to constant weight. The polymer molecular weights ranged from $M_n$=40,000 to 100,000 g/mol with polydispersities <1.5. (Table 2).

Glass transition temperatures measured by DSC are shown in Table 2. The DSC traces also are included as supplementary material. In agreement with the argument that cyclohexyl substituents would increase the rotation barriers of polyglycolide polymers and increase $T_g$, poly(rac-dicyclohexylglycolide) has the highest $T_g$ (98° C.), 43° C. higher than that of poly(rac-lactide). The effects of the cyclohexyl ring on $T_g$ were significant even for the non-symmetrical poly(rac-methylcyclohexylglycolide) ($T_g$=73° C.)

TABLE 3

Properties of Poly(dicyclohexylglycolide)s

| Polymer | $M_n \times 10^{-3}$ | $M_w/M_n$ | $T_g$ (° C.) |
|---|---|---|---|
| poly(rac-dicyclohexylglycolide) | 99.3 | 1.38 | 98 |
| poly(meso-dicyclohexylglycolide) | 89.7 | 1.22 | 96 |
| Poly(R-dicyclohexylglycolide) | 102.5 | 1.42 | 104 |

Somewhat surprising was a $T_g$ of 41° C. for poly(rac-diisopropylglycolide), 14° lower than that of poly(rac-lactide) of comparable molecular weight. The kinetic data shown in FIG. 2 for the polymerization of these monomers suggest that the steric effects of the isopropyl group are close to that of cyclohexyl group and would predict a higher $T_g$ higher than was measured. These data point to the importance of polar groups in polymers chains, such as the intermolecular dipole-dipole interactions and weak C—H ... O hydrogen bonds in polylactides chains (Zhang, J.; Sato, H.; Tsuji, H.; Noda, I.; Ozaki, Y., Macromolecules 2005, 38, 1822). When van der Waals interactions dominate chain-chain interactions, $T_g$ tracks the increase in rotation barriers. For example, polypropylene, poly(3-methyl-1-butene) and poly(cyclohexyl ethylene) have $T_g$s of −40, 50, and 148° C. respectively. (Cao, C.; Lin, Y. J. Chem. Inf. Comput. Sci. 2003, 43, 643 and Zhao, J.; Hanh, S.; Hucul. D.; Meunier, D., Macromolecules 2001, 34, 1737)). When dipole-dipole interactions become important, as the case of polylactides, bulky side chains will not only increase rotation barriers (increase $T_g$), but also interrupt dipole-dipole interactions (decrease $T_g$), by shielding ester groups from each other. Apparently for poly(rac-diisopropylglycolide), the rotation barrier increase caused by the isopropyl groups cannot compensate for the decrease of dipole-dipole interactions, which leads to a lower $T_g$ than poly(rac-lactide).

Figure 3:
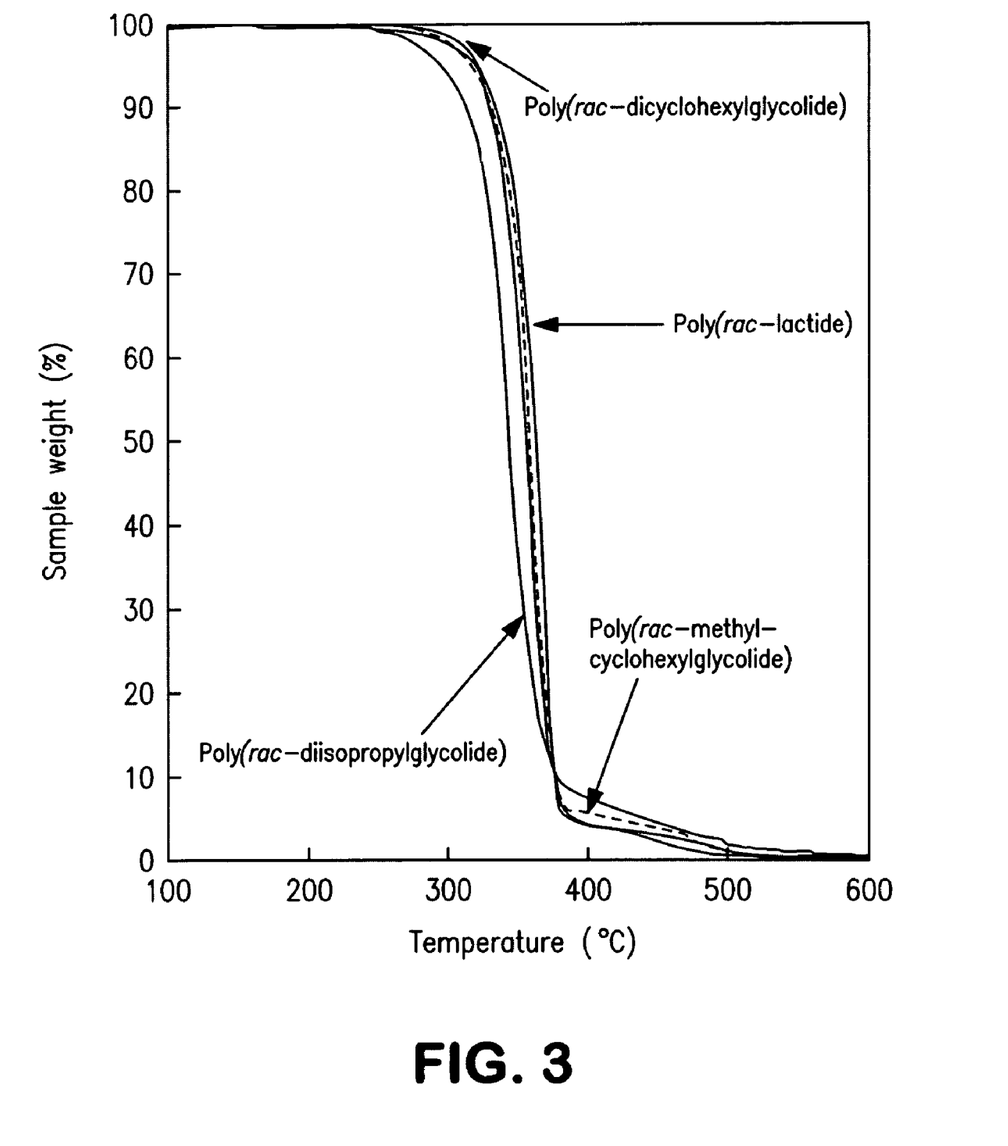
FIG. 3 is a graph showing thermogravimetric analysis results for substituted polyglycolides run in air. Heating rate: 10° C./min.

The decomposition temperatures of polymers measured using thermogravimetric analysis (TGA) define the limiting use temperature of the polymers. As shown in FIG. 3, the TGA traces for the polymers are similar with onsets for weight loss near 300° C. followed by nearly complete weight loss. TGA runs in air and nitrogen show only slight differences in their decomposition curves.

Bulk Polymerization Kinetics. We examined the kinetic behavior of bulk polymerizations of rac-dicyclohexylglycolide because solvent-free polymerizations were used to generate most materials used for characterization. The kinetic data were taken at 200° C. since the monomer melts at >180° C. Bulk polymerizations of rac-dicyclohexylglycolide were carried out by loading monomer with 1 mol % Sn(2-ethylhexanoate)$_2$ and BBA into glass tubes and sealing the tubes under vacuum. The tubes were immersed in a 200° C. bath and removed at desired times. High temperature runs introduce two complications; high polymerization rates make collecting data at low conversions problematic, and because the polymerizations run to high conversions, the polymerization/depolymerization equilibrium must be included in the kinetic analysis (Yin, M.; Baker, G. L., Macromolecules 1999, 32, 7711 and Witzke, D.; Narayan, R., Macromolecules 1997, 30, 7075)). The first order kinetic equation are revised to account for equilibrium monomer concentration $[M]_{eq}$ as shown in equation 2:

$$-\ln\left(\frac{[M]_t - [M]_{eq}}{[M]_0 - [M]_{eq}}\right) = k_p[I]t \qquad (2)$$

Figure 4:
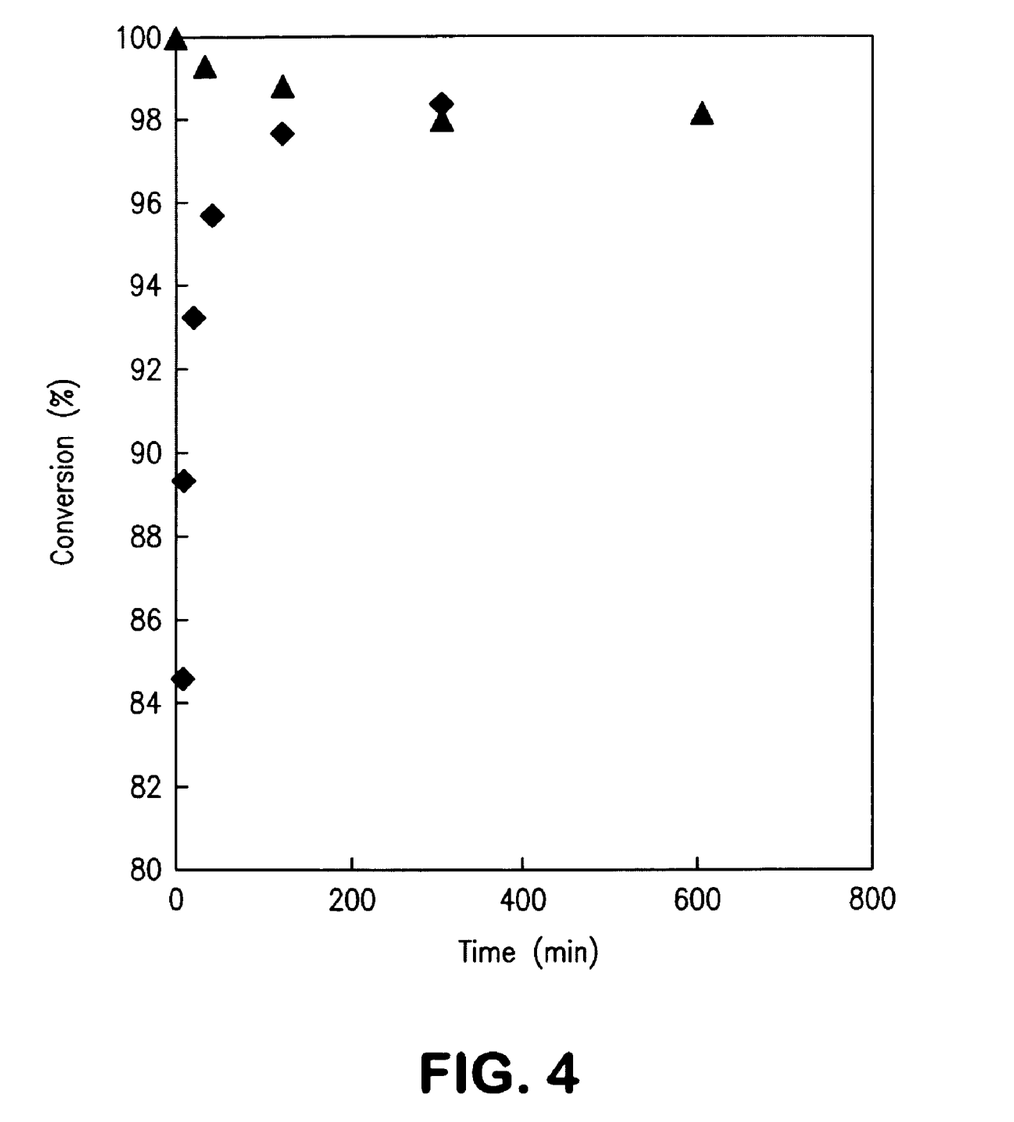
FIG. 4 is a graph showing polymerization/depolymerization data for rac-dicyclohexylglycolide: (♦) polymerization, (▲) depolymerization. Conditions: 200° C., [Sn(2-ethylhexanoate)₂]/[4-tert-butylbenzyl alcohol]=1, [monomer]/[catalyst]=100.

The equilibrium monomer concentration was determined from the limiting conversion reached during 200° C. polymerizations, as well as depolymerization experiments carried out at the same temperature by adding Sn(2-ethylhexanoate)$_2$ to poly(rac-dicyclohexylglycolide) that had been purified by dissolving in $CH_2Cl_2$, washing with HCl, and precipitation into methanol to remove all traces of monomer. Both experiments (FIG. 4) gave ~2% residual monomer, from which we estimate $[M]_{eq}$=0.07M.

Figure 5:
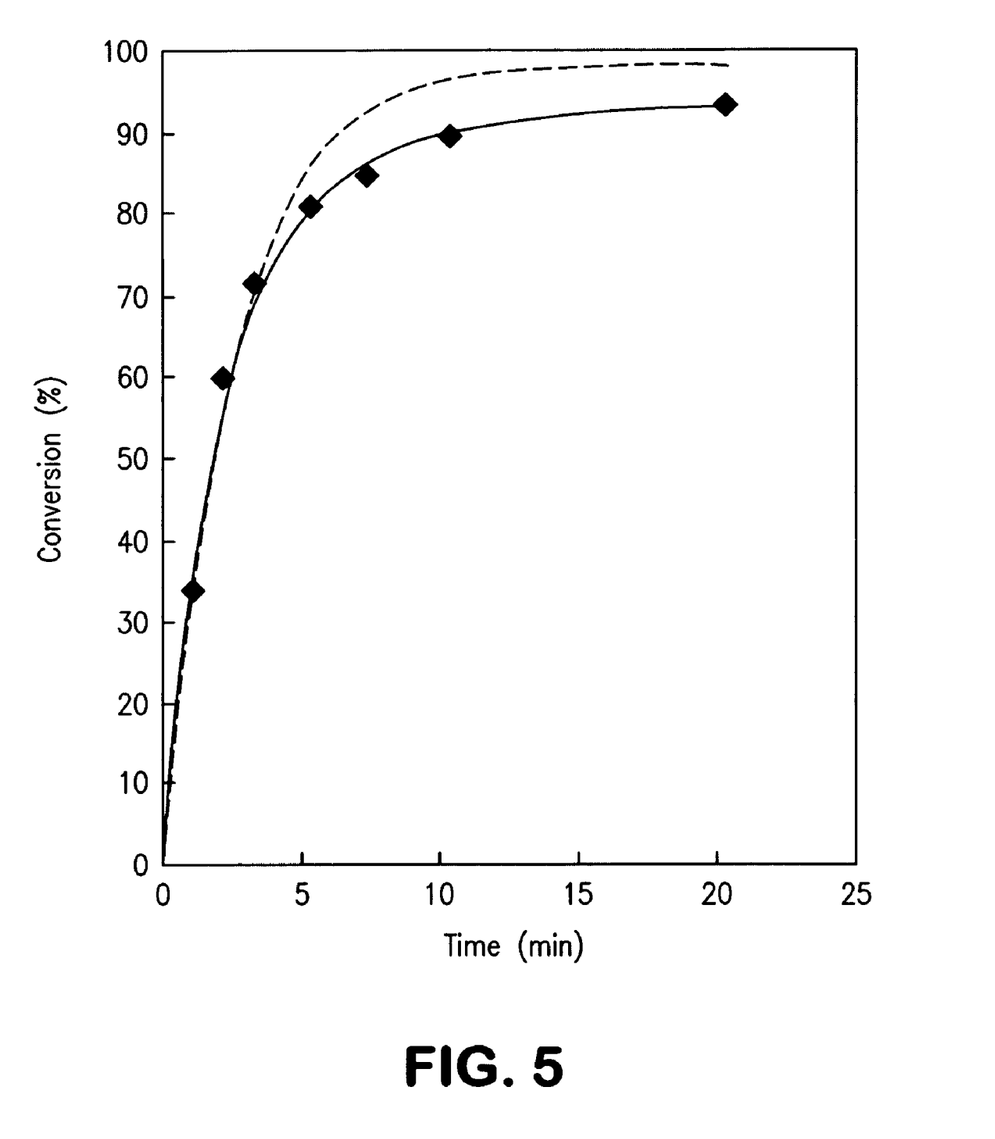
FIG. 5 is a graph showing kinetic data for the bulk polymerization of rac-dicyclohexylglycolide, assuming an equilibrium monomer concentration of 2% (~0.7M). Polymerization conditions: 200° C., [Sn(2-ethylhexanoate)₂]/[4-tert-butylbenzyl alcohol]=1, [monomer]/[catalyst]=100.

The data for the bulk polymerization at of rac-dicyclohexylglycolide are plotted in FIG. 5, assuming 2% residual monomer. The points correspond to the average from three independent runs, except for t=3, 7, and 40, where only two samples were taken. The data are decidedly curved. We suspect that polymerization is sufficiently severe to cause a loss in active chain ends. NMR spectra of polymers after polymerization often show the formation of an aldehyde byproduct. The data can be linearized by assuming that the population of growing chain end decays as $$[I] = [I]_0 e^{-f_d t} \qquad (3)$$

where $k_d$ is the rate constant for the decomposition process. However, the exact mechanism for the loss of chain is unknown.

Figure 6:
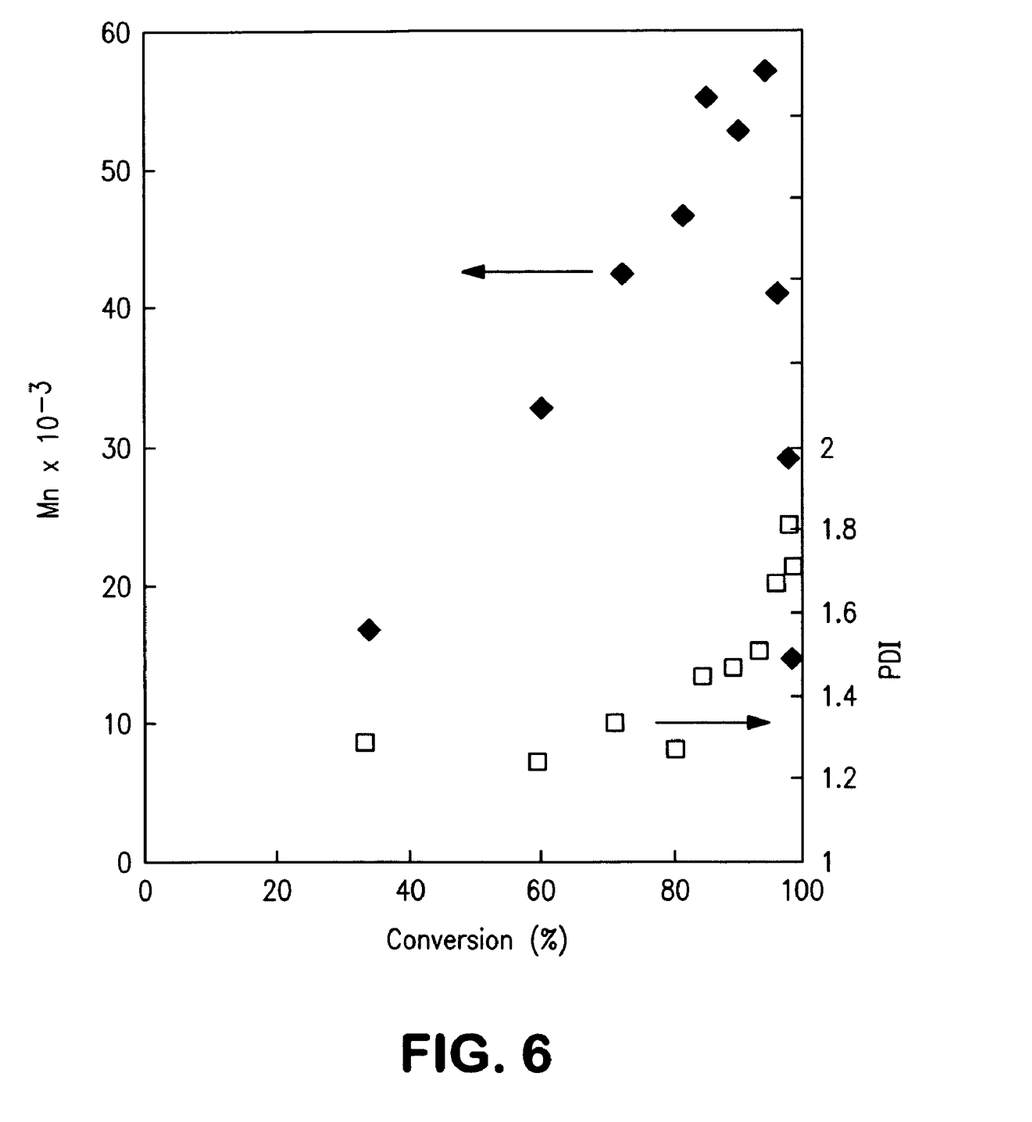
FIG. 6 is a graph showing molecular weight (♦) and polydispersity (□) versus conversion for the bulk polymerization of rac-dicyclohexylglycolide. Polymerization conditions: 130° C., [Sn(2-ethylhexanoate)₂]/[4-tert-butylbenzyl alcohol]=1, [monomer]/[catalyst]=100.

FIG. 6 shows the evolution of the number-average molecular weight ($M_n$) and polydispersity (PDI) with conversion. As the monomer conversion increases during bulk polymerization, $M_n$ increases, reaches a maximum at high conversion, and then decreases. The PDI is nearly constant until 80% conversion, and then increases sharply. This behavior is consistent with the mechanism for ring-opening polymerization of lactides (Yin, M.; Baker, G. L., Macromolecules 1999, 32, 7711). At low conversion, $M_n$ increases linearly with conversion with an almost constant PDI because of the "living" nature of the polymerization. When the monomer is nearly consumed, transesterification becomes competitive with propagation, and the formation of cyclic esters causes a reduction in $M_n$, and an increase in PDI. Obviously, the kinetic data point to degradation as an additional mechanism that can lower $M_n$ and increase PDI (Nishida, H.; Mori, T.; Hoshihara, S.; Fan, Y.; Shirai, Y.; Endo, T., Polym. Degrad. Stab. 2003, 81, 515).

Stereochemical Effects. Polymer stereoregularity that leads to crystallinity is a major factor in determining the physical properties and applications for polylactides (Zell, M.; Padden, B.; Paterick, A.; Thakur, K.; Kean, R.; Hillmyer, M.; Munson, E., Macromolecules 2002, 35, 7700; Chisholm, M.; Iyer, S.; McCollum, D.; Pagel, M.; Werner-Zwanziger, U., Macromolescules 1999, 32, 963; Coudane, J.; Ustariz-Peyret, C.; Schwach, G.; Vert, J., J. Polym. Sci., Polym. Chem. 1999, 35, 1651; Kasperczyk, J. Polymer 1999, 40, 5455; Thakur, K.; Kean, R.; Hall, E.; Kolstad, J.; Munson, E., Macromolecules 1998, 31, 1487; and Thakur, J.; Kean, R.; Hall, J.; Kolstad, J.; Lindgren, T.; Doscotch, M.; Siepmann, J.; Munson, E., Macromolecules 1997, 30, 2422)). In order to understand the consequences of stereoregularity in dicyclohexylglycolides, meso- and R,R-dicyclohexylglycolides were isolated and polymerized. Access to R,R-dicyclohexylglycolides is straight forward since R-(-)-mandelic acid can be hydrogenated directly to R(2R)-(-)-2-cyclohexyl-2-hydroxyacetic acid with retention of configuration. The low melting meso-dicyclohexylglycolide was polymerized at 130° C., while the higher melting R,R-dicyclohexylglycolide required heating to 200° C., the same conditions used for the polymerization of rac-dicyclohexylglycolide. The glass transition temperatures and molecular weights are listed in Table 2. The meso and racemic polymers have $T_g$s of ~98° C., but the $T_g$ of poly(R,R-dicyclohexylglycolide) was noticeable higher, 104° C. The R,R polymer has a specific rotation $[\alpha]_D^{20}$=+23.0° (c=1.0, $CHCl_3$), however, DSC scans and polarized optical microscopy studies of poly(R,R-dicyclohexylglycolide) samples showed no signs of crystallinity.

Figure 7:
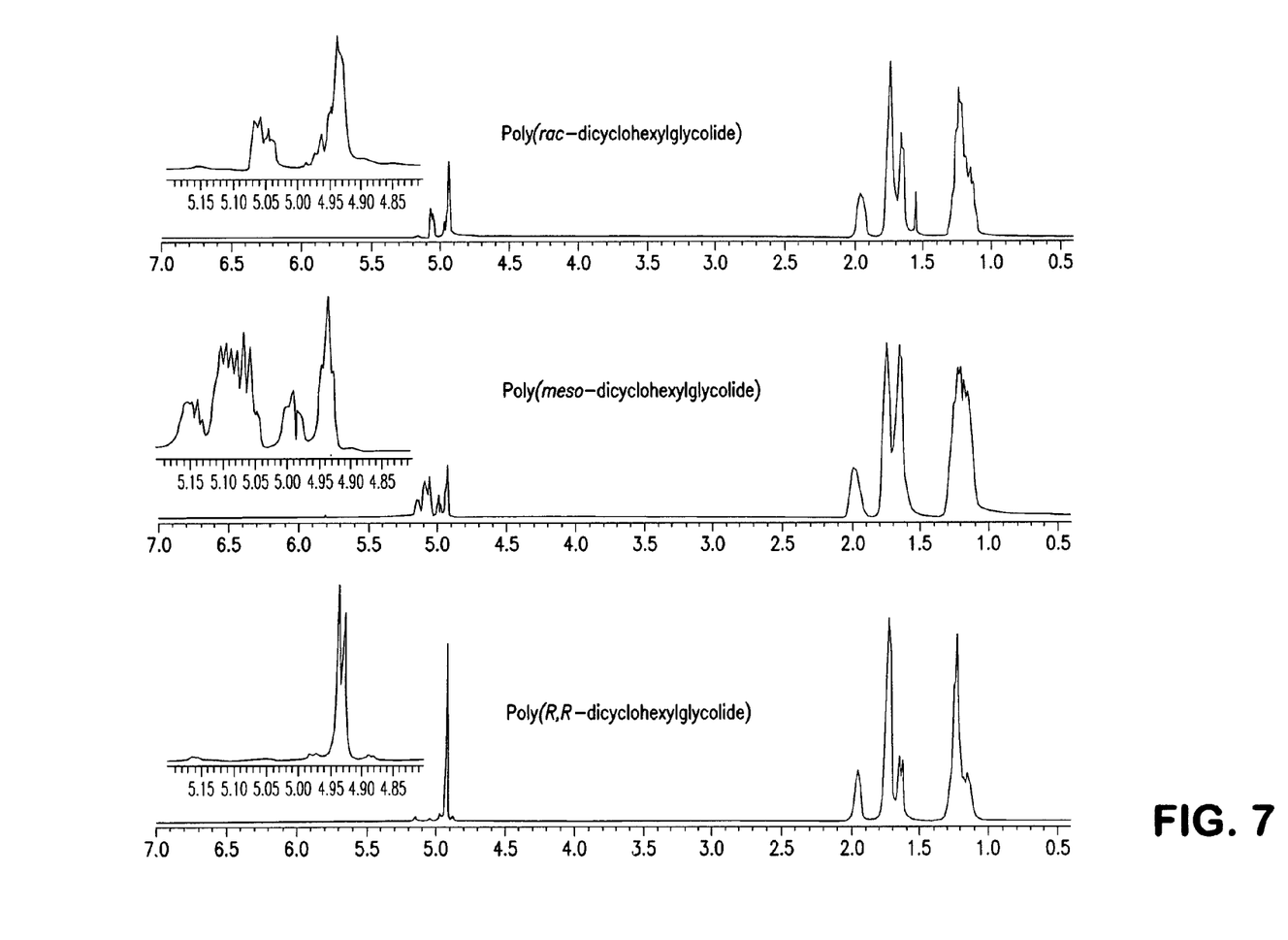
FIG. 7 contains are graphs showing $^1$H NMR spectra for poly(rac-dicyclohexylglycolide), poly(meso-dicyclohexyl glycolide) and poly(R,R-dicyclohexylglycolide).
Figure 8:
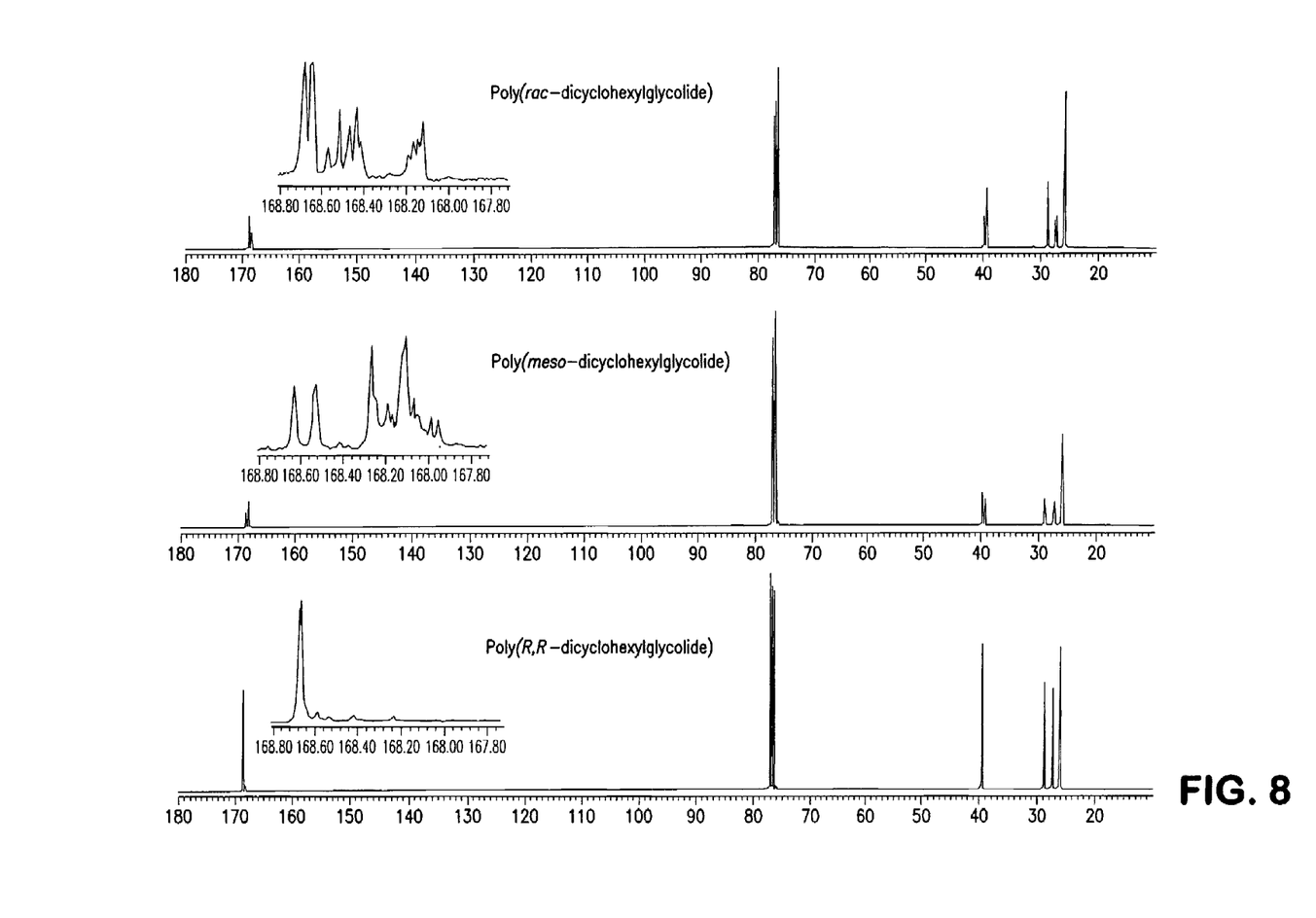
FIG. 8 contains are graphs showing $^{13}$C NMR spectra for poly(rac-dicyclohexylglycolide), poly(meso-dicyclohexyl glycolide) and poly(R,R-dicyclohexylglycolide).

The degree of crystallinity in poly(L-lactide) is largely controlled by the presence of meso and D-lactide impurities, (Drumright, R.; Gruber, P.; Henton, D., Adv. Mater. 2000, 12, 1841) which can be detected by $^1H$ and $^{13}C$ NMR. The $^1H$ NMR and $^{13}C$ NMR spectra of rac-, meso- and R,R-poly (dicyclohexylglycolide) is are shown in FIGS. 7 and 8. An examination of the methine region in the $^1H$ NMR suggests a high degree of stereoregularity. However, small signals at 5.16 and 5.05 ppm suggest possible contamination from meso dyads. The $^{13}C$ NMR spectrum of poly(R,R-dicyclohexylglycolide) is consistent with the $^1H$ NMR data. The $^{13}C$ NMR spectrum is dominated by a singlet at 168.68 ppm, confirming the overall isotactic nature of the polymer, but it too shows minor resonances that imply a population of meso dyads. Integration of the carbonyl region places the isotactic content at 86%. Since the R,R monomer used in these polymerizations was >99% pure, we suspect that epimerization occurs during polymerization. To confirm this notion, we carried out a solution polymerization of the same monomer at 90° C. Integration of the carbonyl region in the $^{13}C$ NMR confirmed increased stereoregularity, with the isotactic resonance corresponding to 98% of the total carbonyl intensity.

EXAMPLES

Unless otherwise specified, ACS reagent grade starting materials and solvents were used as received from commercial suppliers without further purification. $^1H$ NMR analyses were carried out at room temperature on a Varian UnityPlus-500 spectrometer at 500 MHz with the chemical shifts referenced to signals from residual protons in the solvent. $^{13}C$ NMR spectra were obtained on a Varian UnityPlus-500 at 125 MHz. IR spectra were taken with Mattson Galaxy 3000 FT-IR. Elemental analyses were determined using a Perkin-Elmer 2400 CHNS/O Analyzer. Mass spectral analyses were carried out on a VG Masslab Trio-1. Melting points were taken on an Electrothermal capillary melting point apparatus and are uncorrected. Optical rotations were obtained on a Perkin-Elmer 141 polarimeter at 589 nm (sodium D line) using a 1.0 dm cell.

Example 1

Preparation of 2-cyclohexyl-2-hydroxyacetic acid. To a solution of 200 mL methanol were added 38.0 g mandelic-acid, 2.5 mL acetic acid, and 7.5 g rhodium on carbon (5%, Engelhard 5864). The mixture was sealed in an autoclave, purged with nitrogen, and then filled with hydrogen gas. Hydrogenation was carried out at room temperature for 8 hours at 1400 psi hydrogen. The reaction mixture was then removed from the autoclave and filtered. The filtrate was concentrated and recrystallized from toluene. The colorless crystals were collected by filtration and dried under vacuum to give 31.8 g (80.5%) of racemic 2-cyclohexyl-2-hydroxyacetic acid. $^1H$ NMR (DMSO-$d_6$): δ (ppm) 3.71 (d, 1H), 1.66-1.55 (m, 6H), 1.16-1.09 (m, 5H). $^{13}C$ NMR (DMSO-$d_6$): δ (ppm) 175.27, 74.19, 41.15, 28.86, 26.74, 25.84, 25.76, 25.57. IR (KBr): ν ($cm^{-1}$) 3440, 2933, 2856, 1718, 1450, 1280, 1255, 1230, 1103. Anal. Calcd. for $C_8H_{14}O_3$: C, 60.74; H, 8.92. Found: C, 61.12; H, 9.28. mp 135-136° C.

Example 2

Preparation of (R)-(-)-2-cyclohexyl-2-hydroxyacetic acid. To a solution of 200 mL methanol were added 38.0 g of R-(-)-mandelic acid, 2.5 mL acetic acid, and 7.5 g rhodium on carbon (5%, Engelhard 5864). The mixture was sealed in an autoclave, purged with nitrogen, and then filled with hydrogen gas. Hydrogenation was carried out at room temperature for 8 hours at 1400 psi. The reaction mixture was then removed from the autoclave and filtered. The filtrate was concentrated and recrystallized from toluene. The colorless crystals were collected by filtration and dried under vacuum to give 19.8 g of (R)-(-)-2-cyclohexyl-2-hydroxyacetic acid (92.0% yield from 20.7 g R-(-)-mandelic acid). $^1H$ NMR (DMSO-$d_6$): δ (ppm) 3.71 (d, 1H), 1.69-1.52 (m, 6H), 1.16-1.09 (m, 5H). $^{13}C$ NMR (DMSO-$d_6$): δ (ppm) 175.27, 74.19, 41.15, 28.86, 26.74, 25.84, 25.76, 25.57. IR (KBr): ν ($cm^{-1}$) 3442, 2935, 2854, 1716, 1452, 1280, 1261, 1232, 1112, 1099. Anal. Calcd. for $C_8H_{14}O_3$: C, 60.74; H, 8.92. Found: C, 60.89; H, 8.90. mp 124-126° C. $[\alpha]_D^{20}$=-12.0° (c=1.0, $CH_3OH$).

Example 3

Syntheses of rac- and meso-3,6-dicyclohexyl-1,4-dioxane-2,5-dione. A mixture of 0.16 mol of racemic 2-cyclohexyl-2-hydroxyacetic acid and 1.0 g of p-toluenesulfonic acid in 1600 mL toluene was refluxed for 6 days, with the water removed azeotropically via a Dean-Stark trap. Toluene was removed by rotary evaporation and the resulting solid was dissolved in ethyl acetate. The solution was washed with saturated NaHCO$_3$, and dried over MgSO$_4$. After removing ethyl acetate, the crude product was recrystallized from cyclohexane, hexane, or toluene. rac-Dicyclohexylglycolide was recrystallized from toluene, and then cyclohexane. The white crystals were collected by filtration and dried under vacuum to give 4.8 g (21%) of rac-dicyclohexylglycolide. $^1$H NMR (CDCl$_3$): δ (ppm) 4.66 (d, 2H), 2.20-2.12 (m, 2H), 1.86-1.64 (m, 10H), 1.54-1.43 (dq, 2H), 1.37-1.24 (m, 6H), 1.22-1.11 (m, 2H). $^{13}$C NMR (CDCl$_3$): δ (ppm) 166.24, 79.33, 38.82, 28.94, 26.11, 25.75, 25.73 (peaks at 25.75 and 25.73 ppm were resolved to three separate peaks by adding NMR shift reagent europium(III) tris(3-(trifluoromethylhydroxymethylene)-d-camphorate)). IR (KBr): ν (cm$^{-1}$) 2930, 2852, 1758, 1451, 1370, 1303, 1261, 1185, 1111. Anal. Calcd. for C$_{16}$H$_{24}$O$_4$: C, 68.54; H, 8.63. Found: C, 68.73; H, 8.51. MS (EI) m/z 198.1 (100), 123.0 (24), 94.9 (72), 54.9 (41). mp 183-185° C. Meso-Dicyclohexylglycolide was recrystallized from hexane, and then separated from the racemic isomers by column chromatography on silica gel (ether/hexane 1/3) to give 0.86 g (3.8%) desired product. $^1$H NMR (CDCl$_3$): δ (ppm) 4.72 (d, 2H), 2.12-2.03 (m, 2H), 1.86-1.64 (m, 10H), 1.46-1.35 (dq, 2H), 1.34-1.11 (m, 8H). $^{13}$C NMR (CDCl$_3$): δ (ppm) 165.22, 80.59, 80.56, 41.02, 28.57, 26.82, 25.77, 25.54, 25.52. IR (KBr): ν (cm$^{-1}$) 2929, 2852, 1752, 1450, 1379, 1308, 1274, 1110. Anal. Calcd. for C$_{16}$H$_{24}$O$_4$: C, 68.54; H, 8.63. Found: C, 68.93; H, 8.51. MS (EI) m/z 198.1 (100), 123.0 (27), 94.9 (77), 54.9 (54). mp 80.5-81.5° C.

Example 4

Syntheses of (3R,6R)-(+)-3,6-dicyclohexyl-1,4-dioxane-2,5-dione. A mixture of 0.16 mol of (R)-(−)-2-cyclohexyl-2-hydroxyacetic acid) and 1.0 g of p-toluenesulfonic acid in 1600 mL toluene was refluxed for 6 days, with the water removed azeotropically via a Dean-Stark trap. Toluene was removed by rotary evaporation and the resulting solid was dissolved in ethyl acetate. The solution was washed with saturated NaHCO$_3$, and dried over MgSO$_4$. After removing ethyl acetate, the crude product was recrystallized from cyclohexane crude R,R-dicyclohexylglycolide was recrystallized from cyclohexane. The colorless crystals were collected by filtration and dried under vacuum to give 4.5 g R,R-dicyclohexylglycolide (40% yield from 0.08 mol (2R)-(−)-2-cyclohexyl-2-hydroxyacetic acid). $^1$H NMR (CDCl$_3$): δ (ppm) 4.66 (d, 2H), 2.20-2.11 (m, 2H), 1.85-1.65 (m, 10H), 1.53-1.43 (dq, 2H), 1.37-1.24 (m, 6H), 1.22-1.11 (m, 2H). $^{13}$C NMR (CDCl$_3$): δ (ppm) 166.27, 79.27, 38.76, 28.90, 26.07, 25.71, 25.70. IR (KBr): ν (cm$^{-1}$) 2932, 2853, 1760, 1452, 1371, 1302, 1256, 1253, 1185, 1113. Anal. Calcd. for C$_{16}$H$_{24}$O$_4$: C, 68.54; H, 8.63. Found: C, 68.78; H, 8.67. MS (EI) m/z 198.1 (100), 123.0 (25), 94.9 (75), 54.9 (44). mp 194-196° C. [α]$_D^{20}$=+190.0° (c=1.0, CHCl$_3$).

Example 5

Synthesis of 3-cyclohexyl-6-methyl-1,4-dioxane-2,5-dione. To a 500 mL 3-neck flask were added 12.66 g (0.08 mol) of 2-cyclohexyl-2-hydroxyacetic acid, 0.096 mol of α-bromopropionyl bromide, and 200 mL THF. The flask was purged with nitrogen and then cooled in a salt-ice bath. A mixture of 14.5 mL Et$_3$N and 50 mL THF was added dropwise under mechanical stirring and the solution was cooled and stirred overnight. The solution was filtered to remove a white solid, and the filtrate was evaporated to dryness. The solid was dissolved in ethyl acetate. The solution was washed with 2 M HCl (3×100 mL), saturated NaCl, dried over MgSO$_4$, and then concentrated to give a solution of the crude linear acid ester. The viscous liquid was mixed with 1600 mL acetone and 27 g NaHCO$_3$, and refluxed for 2 days. The solids were removed by filtration and the acetone was evaporated to dryness. The crude product was dissolved in ethyl acetate, dried over MgSO$_4$, and the ethyl acetate was removed by rotary evaporation. The crude product was recrystallized from cyclohexane, and the colorless crystals were collected by filtration and dried under vacuum to give 10.0 g (59%) of rac-methylcyclohexylglycolide. $^1$H NMR (CDCl$_3$): δ (ppm) 4.97 (q, 1H), 4.71 (d, 1H), 2.20-2.12 (m, 1H), 1.86-1.64 (m, 8H), 1.54-1.44 (dq, 1H), 1.38-1.25 (m, 3H), 1.23-1.12 (m, 1H). $^{13}$C NMR (CDCl$_3$): δ (ppm) 167.50, 166.02, 79.64, 72.12, 38.68, 28.93, 26.09, 25.74, 15.99. IR (KBr): ν (cm$^{-1}$) 2999, 2939, 2853, 1763, 1761, 1451, 1379, 1341, 1296, 1245, 1184, 1098. Anal. Calcd. for C$_{11}$H$_{16}$O$_4$: C, 62.25; H, 7.60. Found: C, 62.34; H, 7.67. MS (EI) m/z 129.9 (100), 83.0 (10), 56.0 (13), 55.0 (26). mp 80.5-82.0° C. The cis relationship of the methyl and cyclohexyl groups on the glycolide ring was verified by 1D Gradient-Selected Transient Nuclear Overhauser Effect Experiment (NOESY1D).

Example 5

Solution Polymerization of Substituted Glycolides. A Schlenk flask containing 2.0 mmol of substituted glycolide and a magnetic stir bar was fitted with a septum and then evacuated and refilled with argon three times. Predetermined amounts of anhydrous toluene, and toluene solutions of Sn(2-ethylhexanoate)$_2$ and 4-tert-butylbenzyl alcohol (BBA) were then added via syringe through the septum to yield a 0.2 M monomer concentration. The Schlenk flask was then suspended in a 90° C. oil bath to initiate polymerization. For kinetic studies, a syringe was used to remove aliquots of the reaction solution at specific intervals and were analyzed by NMR to determine the monomer conversion. The molecular weights of polymers were determined by Gel Permeation Chromatography (GPC) using a PLgel 20 m Mixed A column and a Waters 2410 differential refractometer detector at 35° C. THF was used as the eluting solvent at a flow rate of 1 mL/min, and monodisperse polystyrene standards were used to calibrate the molecular weights. Differential Scanning Calorimetry (DSC) analyses of the polymers were obtained using a TA DSC Q100. Samples were run under a nitrogen atmosphere at a heating rate of 10° C./min, with the temperature calibrated with an indium standard. Thermogravimetric analyses (TGA) were run both in air and under nitrogen at a heating rate of 10° C./min using a Perkin-Elmer TGA 7.

Example 6

Bulk Polymerization of Substituted Glycolides. Solvent-free polymerizations were carried out in sealed ampoules prepared from ⅜ in. diameter glass tubing. After charging with substituted glycolide and a stir bar, an ampoule was connected to a vacuum line through a vacuum adapter. After evacuating the ampoule for 2 hours, the ampoule was filled with argon, and a syringe was used to add a predetermined amount of the Sn(2-ethylhexanoate)$_2$ and BBA solutions to the ampoule through the adapter. The solvent was removed in vacuo, and the ampoule was flare-sealed and immersed in oil bath. At the end of the polymerization, the ampoule was cooled and opened, and the polymer was dissolved in dichloromethane. A portion of the sample was evacuated to dryness and analyzed by NMR for conversion. The rest of polymer solution was precipitated three times from cold methanol, washed with dilute HCl in CH$_2$Cl$_2$ solution, and then precipitated from cold methanol once again to completely remove residual monomer and catalysts.

Polylactides substituted with cyclohexyl and isopropyl groups were successfully synthesized by ring opening polymerization of the substituted glycolides with Sn(2-ethylhexanoate)$_2$ and 4-tert-butylbenzyl alcohol. For rac-dicyclohexylglycolide polymer, the T$_g$ is 44° C. higher than that of poly(rac-lactide). Even poly(rac-methylcyclohexylglycolide), with one cyclohexyl group per repeat unit, has a T$_g$ at 73° C. The high T$_g$s result from polymer backbones that are rigidified by the bulky cyclohexyl groups. Solution polymerizations show that the steric demands of glycolide substituents decrease with cyclohexyl>isopropyl>methyl.

The effects of stereosequence distributions on polymer properties were studied. Poly(R,R-dicyclohexylglycolide) synthesized from the optically pure R,R-dicyclohexylglycolide has a relatively high T$_g$ (104° C.), and shows optical rotation. Poly(rac-dicyclohexylglycolide) and poly(meso-dicyclohexylglycolide) show very similar thermal properties, even though their stereosequence distributions are irregular.

Polylactides are degradable polymers used for medical applications as well as packaging materials, and fibers. The glass transition temperatures of polylactides are generally below 50° C., requiring that polylactides to be crystalline for dimensional stability. New polylactides were invented that mimic polystyrene with glass transitions as high as 104° C.

The high glass transition of these polymers (>90° C.) expand applications for degradable polymers from renewable resources, especially as packaging materials. Medical applications also are likely for this "green polystyrene".

The preferred polymers have the structure

Structure 1

Where n is greater than 20. Preferably the glass transition temperature is greater than 20° C.

Another preferred polymer has the structure

Structure 2 where n is greater than 20. Included are:

1. The polymer of Structure 2, where R$_1$ is a linear or branched alkyl chain of 1-6 carbon atoms.

2. The polymer of Structure 2 having a glass transition temperature greater than 70° C.

3. The polymer of Structure 2 where the R$_1$ group is H.

4. The polymer of Structure 2 where the R$_1$ group is CH$_3$.

5. The polymer of Structure 2 where the R$_1$ group is isopropyl.

6. The polymer of Structure 2, where the carbon atoms linking the cyclohexyl group to the polymer backbone are stereoregular.

7. The polymer of Structure 2, where the stereochemistry at each carbon atom linking cyclohexyl groups to the polymer backbone is R isomeric.

8. The polymer of Structure 2, where the stereochemistry at each carbon atom linking cyclohexyl groups to the polymer backbone is S isomeric.

9. The polymer of Structure 2, where the carbon atoms linking R groups to the polymer backbone are stereoregular.

10. The polymer of Structure 2 where the stereochemistry at each carbon atom linking R$_1$ to the polymer backbone is R isomeric.

11. The polymer of Structure 2, where the stereochemistry at each carbon atom linking R$_1$ to the polymer backbone is S isomeric.

12. The polymer of claim Structure 2 where the R$_1$ group is methyl, which is prepared by the polymerization of methylcyclohexylglycolide.

13. The polymer of Structure 2 where R$_1$ group is isopropyl, which is prepared by the polymerization of isopropylcyclohexylglycolide.

14. The polymer of Structure 2 where R$_1$ group is ethyl, which is prepared by the polymerization of ethylcyclohexylglycolide.

Another polymer is for instance

Structure 3 where n and m are greater than 20.

The polymers can be prepared by the copolymerization of dicyclohexyl glycolide with one or more glycolides selected from the group of glycolide, lactide, mandelide, isopropylglycolide, and glycolides substituted with linear or branched alkyl groups of 6 or less carbon atoms.

The present invention includes tactic polymers, stereo regular polymers, isotactic polymers, syndiotactic polymers, atactic polymers, graft macromolecules and stereo block macromolecules as defined in Pure and Applied Chemistry 68, 2287-2311 (1996) and Pure Applied Chemistry 53, 733-752 (1981).

It is intended that the foregoing description be only illustrative of the present invention and that the present invention be limited only by the hereinafter appended claims.

We claim:

1. A glycolide compound of the formula:

wherein:

R is selected from the group consisting of lower alkyl containing 1 to 8 carbon atoms and cycloalkyl containing 3 to 8 carbon atoms, where R optionally is substituted with a first passive substituent, and $R_1$ is hydrogen or a second passive substituent.

2. The compound of claim 1 wherein R is cyclohexyl and $R_1$ is hydrogen.

3. The compound of claim 1 wherein R is methyl or isopropyl, and $R_1$ is hydrogen.

4. The compound of claim 2 wherein R is cyclohexyl as an RR-dicyclohexylglycolide enantiomer.

5. The compound of claim 2 wherein R is cyclohexyl as an SS dicyclohexylglycolide enantiomer.

6. The compound of claim 2 wherein R is cyclohexyl as racemic RS dicyclohexylglycolide.

7. The compound of claim 1 selected from the group consisting of RR, SS and RR isomers.

8. The compound of claim 2 selected from the group consisting of RR, SS and RS isomers.

9. The compound of claim 3 selected from the group consisting of RR, SS and RS isomers.

* * * * *

UNITED STATES PATENT AND TRADEMARK OFFICE
CERTIFICATE OF CORRECTION

PATENT NO. : 7,709,596 B2  Page 1 of 1
APPLICATION NO. : 12/583635
DATED : May 4, 2010
INVENTOR(S) : Gregory L. Baker, Feng Jing and Milton R. Smith, III It is certified that error appears in the above-identified patent and that said Letters Patent is hereby corrected as shown below:

Column 10, line 56, " $[I] = [I]_0 e^{-f_d t}$ " should be -- $[I] = [I]_0 e^{-k_d t}$ --.

Signed and Sealed this

Seventeenth Day of August, 2010

David J. Kappos
*Director of the United States Patent and Trademark Office*